United States Patent [19]

Berenbaum et al.

[11] 4,072,027

[45] Feb. 7, 1978

[54] STABILIZED HEAT ACTIVATED HEAT EXCHANGE ABSORPTION PAIR

[75] Inventors: Morris B. Berenbaum, Summit, N.J.; Francis E. Evans, Hamburg, N.Y.; Richard E. Eibeck, Orchard Park, N.Y.; Martin A. Robinson, East Amherst, N.Y.

[73] Assignee: Allied Chemical Corporation, Morris Township, N.J.

[21] Appl. No.: 760,489

[22] Filed: Jan. 19, 1977

[51] Int. Cl.$^2$ .................. C09K 5/04; F25B 15/02
[52] U.S. Cl. ........................................ 62/112; 252/68; 252/69; 252/389 A; 252/400 A
[58] Field of Search ............... 252/67, 68, 69, 389 A, 252/400 A; 62/112

[56] References Cited

U.S. PATENT DOCUMENTS

| | | | |
|---|---|---|---|
| 3,459,660 | 8/1969 | Shepherd | 252/68 X |
| 3,558,470 | 1/1971 | Gillespie et al. | 252/68 X |
| 3,645,886 | 2/1972 | Gillespie et al. | 252/68 X |
| 4,005,584 | 2/1977 | Li | 62/112 |

*Primary Examiner*—Harris A. Pitlick
*Attorney, Agent, or Firm*—Alan M. Doernberg; Jay P. Friedenson

[57] ABSTRACT

A stabilized heat exchange medium is disclosed including a fluorocarbon, an absorbant and a tribasic phosphite stabilizer. The preferred absorbants are assymetrical furan derivatives containing at least 1 oxygen with a single bond to an adjacent carbon, and is most preferably an alkyl tetrahydrofurfuryl ether. The fluorocarbon contains 1 or 2 carbons, 1 or 2 hydrogens and the remainder chlorine and fluorine. The tribasic phosphites are of the formula $(R_1'O)(R_2'O)(R_3'O)P$, wherein $R_1'$, $R_2'$ and $R_3'$ are each independently alkyl, alkenyl, phenyl, alkylene phenyl, alkylene alkylphenyl or alkylphenyl.

24 Claims, No Drawings

STABILIZED HEAT ACTIVATED HEAT EXCHANGE ABSORPTION PAIR

CROSS-REFERENCE TO RELATED APPLICATIONS

Chien C. Li, "Composition, Method and Apparatus for Absorption Heat Pump," Ser. No. 567,043, filed Apr. 10, 1975 now U.S. Pat. No. 4,005,584;

Henry R. Nychka et al., "Composition, Methods and Apparatus for Absorption Heating and Refrigeration," Ser. No. 567,044, filed Apr. 10, 1975 now U.S. Pat. No. 4,042,524.

BACKGROUND OF THE INVENTION

Absorption heat pumps are known wherein a refrigerant (such as ammonia) is dissolved in a solvent or absorbant (such as water) and, in well known thermodynamic steps, successively boiled off in a generator, condensed, evaporated and reabsorbed into a weak solution of the absorbent, to provide refrigeration by heat exchange with the condensor of the cycle. Operation of such a system is described in J. H. Perry (R. H. Perry et al. editors), CHEMICAL ENGINEER'S HANDBOOK (New York 1963) pp. 12-10 through 12-12.

Among the absorption pairs considered to replace ammonia water have been certain furan derivatives as absorbant and certain fluorocarbons as refrigerant. Examples are found in Ser. Nos. 567,043 and 567,044 referenced above, as well as the following patents of Zellhoefer: U.S. Pat. Nos. 2,040,898, 2,040,901, 2,040,902, 2,040,905, 2,040,909. While these are good absorption pairs for refrigeration and heating, the maximum possible efficiencies cannot be achieved without a high generator temperature. At such temperatures above about 150° C, particularly over the 5-20 year expected life of absorption pairs, reactions begin to occur creating corrosive side products such as HCl and HF, unacceptable in a heat pump.

BRIEF DESCRIPTION OF THE INVENTION

The invention includes, as a composition of matter, a fluorocarbon selected from monochlorodifluoromethane, dichloromonofluoromethane, trifluoromethane, monochloromonofluoromethane, monochlorotetrafluoroethane, monochlorotrifluoroethane and mixtures thereof; an assymetrical furan derivative of the formula

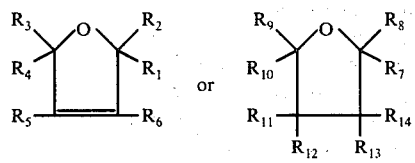

where $R_1$–$R_{14}$ are each independently H, alkyl having 1–5 carbons, alkoxy having 1–5 carbons, alkylene phenyl having 7–11 carbons, a hydroxy alkyl having 1–5 carbons, alkoxy alkyl of from 2–6 carbons, lower alkylene carboxylate having 2–6 carbons, alkyl carboxylate having 2–6 carbons, fluorine or chlorine, provided that at least one substituent has an oxygen atom which has a single bond to a carbon atom or mixtures thereof; and an effective amount of a stabilizer of the formula $(R_1'O)(R_2'O)(R_3'O)P$, wherein $R_1'$, $R_2'$, and $R_3'$ are each independently alkyl, alkenyl, phenyl, alkylene phenyl, alkylene alkylphenyl or alkylphenyl.

The invention also includes a method of absorption heating which comprises releasing heat of solution in the vicinity of an area to be heated by absorbing a fluorocarbon in an asymmetrical furan derivative containing a stabilizer to form the above composition, heating the resultant solution to release the fluorocarbon from the furan derivative, condensing released fluorocarbon in the vicinity of the area to be heated to form the liquid fluorocarbon, evaporating the liquid fluorocarbon at a location removed from the vicinity to be heated and returning the evaporated fluorocarbon to the vicinity of the area to be heated for reabsorption into the furan derivative.

DETAILED DESCRIPTION OF THE INVENTION

The invention includes an improved composition of matter suitable for use as the heat exchange medium in a heat activated heat pump. Examples of such systems are disclosed in a co-pending application of Chien C. Li, entitled "Composition, Method and Apparatus for Absorption Heating," Ser. No. 567,043, filed Apr. 10, 1975 which is incorporated herein by reference. That application describes an absorption pair consisting of a lower alkyl fluorocarbon solute dissolved in a furan derivative absorbant, a method of absorption heating utilizing such compositions and a novel furan derivative. In the present application, absorption pairs including such a lower fluorocarbon, such a furan derivative absorbant and a tribasic phosphite stabilizer are included in the invention.

Suitable fluorocarbon solutes for the present compositions include methyl and ethyl derivatives having at least one and preferably one or two, hydrogens, at least one fluorine and the remainder chlorine. Especially preferred are the fluorocarbons designated fluorocarbons R-21, R-22, R-23, R-31, R-123, R-124 and R-133 as illustrated in the examples that follow. Any isomer or mixture of isomers of the latter three could be used. Nevertheless, the preferred isomers are $CHCl_2CF_3$ (R-123), $CHClFCF_3$ (R-124) and $CH_2ClCF_3$ (R-133a). Most preferred is dichloromonofluoromethane (R-21). It is believed that each of these fluorocarbons, having a hydrogen and a fluorine on the same carbon, exhibit excellent hydrogen bonding properties between the hydrogen of the fluorocarbon and at least one oxygen of the absorbant. Such hydrogen bonding properties increase the heat of absorption, and thus the heat capacity of a system using such compositions.

The preferred absorbants are specifically disclosed in copending application Ser. No. 567,043, and can be best illustrated by the following two formulas

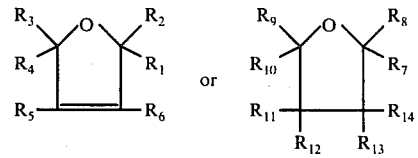

In these formulas $R_1$–$R_{14}$ are each, independently, H, lower alkyl, phenyl, lower alkylene phenyl, hydroxy containing lower alkyl, alkoxy alkyl, lower alkylene carboxylate, fluorine or chlorine, provided that at least one substituent on the ring has an oxygen atom which has a single bond to a carbon atom. In general, saturated ring compounds are preferred for high temperature operation. Among the most preferred absorbents are those of the formula

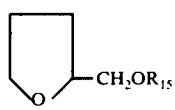

wherein $R_{15}$ is alkyl have 1 to 5 carbons, and preferably 2 to 4 carbons and the remaining substituents are hydrogen. Such compounds, referred to as tetrahydrofurfuryl ethers, have previously been found to exhibit good heat exchange properties when combined with one of the above fluorocarbons. However, particularly with the ethyl, t-butyl and n-butyl tetrahydrofurfuryl ethers, the above two-component compositions exhibit some decomposition upon prolonged exposure to high temperatures. Thus the present invention provides for a third component in the form of a tribasic phosphite stabilizer which, among several classes of known stabilizers, alone exhibit the ability to stabilize the above fluorocarbon in combination with the above furan ring containing compound. In the absence of such stabilizer, upon prolonged exposure to high temperatures, reactions occur including the splitting of the furan derivative at one of its oxygens and the reaction of the fluorocarbon at one of its halogens to form HCl or HF. Such products are particularly corrosive and harmful in a metal-walled heat exchange system, and thus must be avoided in order to provide a system with a long absorbant pair life.

The preferred phosphite stabilizers are of the formula $(R_1'O)(R_2'O)(R_3'O)P$, wherein $R_1'$, $R_2'$ and $R_3'$ are each, independently, aryl, alkylaryl or alkyl. The size of the constituents $R_1'$, $R_2'$ and $R_3'$ is not critical in terms of stabilizer properties, as it is believed that the phosphite is the active group in stabilization. For example R' groups of 1-20 carbons can be used, with 6-14 more preferred. These include the phosphites $(R_1'O)(R_2'O)(R_3'O)P$ wherein $R_1'$, $R_2'$ and $R_3'$ each have 1-20 carbons, and most preferably 6-14 carbons. Exemplary preferred $R_1'$, $R_2'$ and $R_3'$ groups are alkyl having 6-14 carbons, phenyl, alkylphenyl having 7-14 carbons, alkylene phenyl having 7-14 carbons or alkylene alkylphenyl having 8-14 carbons. By alkalene phenyl is meant $-(CH_2)_n$ phenyl; by alkylphenyl is meant -phenyl- $(C_mH_{2m+1})_n$; by alkalene alkylphenyl is meant $(CH_2)_n$-phenyl-$(C_mH_{2m+1})_n$. Among the preferred tribasic phosphite stabilizers illustrated in the Examples are those with $R_1'$, $R_2'$ and $R_3'$ independently as isodecyl or phenyl, with triisodecyl phosphite being exemplary.

However, the size of the substituents can be altered in order to provide a suitable boiling point in order to maintain the phospite stabilizer in a specific liquid or vapor phase in a heat exchange system. For many applications, a phosphite which remains primarily or almost exclusively in the liquid phase in a generator operating at up to about 400° F is preferred. Accordingly, higher molecular weight tribasic phosphites such as triphenyl phosphite, tridecyl phosphite, trisnonyl phosphite, tristearyl phosphite, trilaurel phosphite, triisooctyl, phosphite, triisodecyl phosphite, and the like are preferred. Such tribasic properties are well known articles of commerce with several being sold by Borg Warner Chemicals of Parksburg, W. Va. under the WESTON trademark. Such phosphites are prepared, as is well known in the art, by reactions between $PCl_3$ with the alcohol corresponding to each substituent group to form the tribasic phosphite, as for example: $PCl_3 + 3ROH \rightarrow (RO)_3P + 3HCl$. In U.S. Pat. No. 3,459,662 it is stated that phosphite esters $(R_1O)(R_2O)(R_3O)P$ are readily prepared by the interaction of phosphorus trihalide ($PCl_3$ or $PBR_3$) (1 mol) with 3 mols of ROH. Of course mixtures of phosphites will be obtained if heterogenous alcohol reactants are used, and, if desired they can be separated on a column. In many reactions it is preferred to use a base to remove by-product HCl and prevent side reactions, with preferred basis including dimethylaniline and pyridine. Several other suitable esters of phosphorous acids are listed in R. C. Weast, HANDBOOK OF CHEMISTRY AND PHYSICS (57th Edition 1976), pages C-435 through C-436 as compounds p797 through p807, and in G. M. Kosolapoff and L. Maier, ORGANIC PHOSPHOROUS COMPOUNDS, volume 5(New York 1973).

Neither the amount of fluorocarbon solute or refrigerant nor the amount of phosphite stabilizer are particularly critical. Nonetheless between about 4 and about 60% by weight, and more preferably between about 10 and about 40% of fluorocarbon by weight of furan derivative absorbant or solvent is preferred to give best thermodynamic properties. The effective range of phosphite stabilizer will vary somewhat depending on the particular stabilizer, fluorocarbon and solvent. The only upper limit is that amounts should not be used which adversely effect the thermodynamic and other properties of the absorbant pair. Nevertheless about 0.05 to about 3.0% stabilizer by weight of furan derivative solvent is generally adequate with about 0.05 to about 1.0 being most preferred. Amounts well below the saturation amounts of refrigerant and stabilizer in the solvent are preferred, but this limit is not normally reached unless the $R_{1-6}$ or $R_{7-14}$ or $R_1'$-$R_3'$ groups are quite large. Ethyl tetrahydrofurfuryl ether, ETFE, for example, will easily dissolve the entire preferred weight ratio range of most tribasic phosphite stabilizers.

In the method of the invention as described above the term "vicinity of the area to be heated" includes both the physical vicinity and remote physical locations provided a heat transfer fluid (typically water) circulates between the condensing or absorbing location and the space to be heated. For example, circulating water can conduct heat from the absorber and condenser of a heat pump outside a house to either the interior rooms or to another heat exchanger where air is heated before being blown into the rooms.

The preferred furan derivatives for practice of the method are the alkyl tetrahydrofurfuryl ethers, with alkyl having 1-5 carbons, preferably 2-4 carbons and most preferably being ethyl or t-butyl. The preferred phosphite stabilizers are, as described above, those wherein $R_1'$, $R_2'$ and $R_3'$ each have 1-20 carbons.

As can be seen in the examples that follow, tribasic phosphite stabilizers provide stability for prolonged periods at high temperatures for the pairs consisting of fluorocarbons and furan derivatives of the present invention. It should be appreciated that stabilization under high temperatures for several months would correspond to many years of life in a heat pump system wherein any one aliquot of mixture is exposed to such high temperatures only when the heat pump is operating, and then only during a small portion of the cycle. For example, the heat exchange medium in the form of a rich liquor containing the high percentage of fluorocarbon would be subject to such high temperatures in the generator portion only, and would quickly be cooled by heat exchange with incoming rich liquor during passage out of the generator portion of the heat exchanger.

EXAMPLES

Examples 1-8 and Comparisons 9-40

Thirty-seven Pyrex tubes were filled at liquid nitrogen temperatures with a mixture by weight of 85 percent ethyl tetrahydrofurfuryl ether (referred to as ETFE) and 15 percent dichloromonofluoromethane (referred to as fluorocarbon 21). In these tubes high purity ETFE was used (about 99.6% by weight with the remainder tetrahydrofurfuryl alcohol (THFA). An aluminum alloy rod (aluminum 1100) was inserted into each tube. To each of the first 32 tubes was added about 0.1 percent by weight of a compound from group A:

Group A (A1) triphenyl phosphite
(A2) butylated hydroxytoluene (BHT)
(A3) dimethyl phthalate
(A4) triethylene tetramine To each of tubes 1-7, 9-14, 17-24, 26-31 and 31-37 were added about 0.1 percent by weight of a compound selected from group B:

Group B (B1) 2-nitropropane
(B2) 1-decene
(B3) n-butyl disulfide
(B4) cyclohexanol
(B5) phenyl glycedyl ether Each of the compounds of group A is known to have antioxidant properties in at least some environments. Each of the compounds of group B is known to have anticorrosive properties in at least some environments. The contents each tube are illustrated in the Table 1:

9-40 had exploded. The recovered aluminum alloy rods all demonstrated severe pitting.

Each of the remaining tubes 1-8 and 41-45 were opened and analyzed. None of the aluminum rods showed severe pitting and only tubes 1 and 5 were discolored. Only tube 1 exhibited severe discoloring. Tubes 6 and 7 were lightest in color, tubes 2, 3 and 4 were lowest in free chloride ion and tube 6 was lowest in free fluoride ion. Using gas chromatography, each of the experimental tubes with triphenyl phosphite (additive A1) showed levels of the expected degradation products about as low as the room temperature samples (tubes 41 and 42). Such degradation products included other fluorocarbons, water, ethanol, diethylether and miscellaneous trace materials. In each of tubes 2-8, at least 82% by volume of the sample is observed to be ETFE, similar to the value of 82.2% for tube 41, a room temperature control. The highest values of ETFE were 83.9% for tube 2, 84.2% for tube 6 and 84.5% for tube 8, wherein the only additive was triphenyl phosphite.

EXAMPLES 46-48

Comparison with Commercial Stabilizers

Three tubes were prepared with 80% ETFE and 20% fluorocarbon 21. A commercial antioxidant and thermal stabilizer sold by Ciba-Geigy as IRGANOX 1010 and described in U.S. Pat. Nos. 3,285,855 and 3,644,482 was added at 0.1% by weight, with a mixture at liquid nitrogen temperature. The tubes were sealed and gradually heated to 230°-235° C. Although each tube was initially bright and clear, by the end of one week all three tubes had exploded. Thus, this high molecular weight stabilizer did not perform as well as the tribasic phosphites.

EXAMPLES 49-132 and Controls 133-158

Ninety-two more tubes were prepared with 80% ETFE (low or high purity as described below) and 20% fluorocarbon 21 as in Examples 1-8. These phosphite additives were tested on an equivalent molar basis, with

TABLE 1

| Examples | Additives | Comparisons | Additives | Comparisons | Additives | Comparisons | Additives | Comparisons | Additives |
|----------|-----------|-------------|-----------|-------------|-----------|-------------|-----------|-------------|-----------|
| 1 | A1,B1 | 9 | A2,B1 | 17 | A3,B1 | 26 | A4,B1 | 33 | B1 |
| 2 | A1,B2 | 10 | A2,B2 | 18 | A3,B1 | 27 | A4,B2 | 34 | B2 |
| 3 | A1,B2 | 11 | A2,B3 | 19 | A3,B2 | 28 | A4,B3 | 35 | B3 |
| 4 | A1,B2 | 12 | A2,B3 | 20 | A3,B3 | 29 | A4,B4 | 36 | B4 |
| 5 | A1,B3 | 13 | A2,B4 | 21 | A3,B4 | 30 | A4,B5 | 37 | B5 |
| 6 | A1,B4 | 14 | A2,B5 | 22 | A3,B4 | 31 | A4,B5 | | |
| 7 | A1,B5 | 15 | A2 | 23 | A3,B4 | 32 | A4 | | |
| 8 | A1 | 16 | A2 | 24 | A3,B5 | | | | |
| | | | | 25 | A3 | | | | |

Several tubes (38, 39, 40, 41) were then prepared using the same weight ratio of 85% ETFE and 15% fluorocarbon 21, but with no additives. Controls were prepared with ETFE only (tubes 42 and 43) and fluorocarbon 21 only (tubes 44 and 45). Each of tubes 1-40, 43 and 45 were sealed and gradually heated to 30°-235° C (about 450° F) and maintained there for 4 weeks. Tubes 41, 42 and 44 were sealed and kept at room temperature for the same period.

On initial observation after 2 weeks, tubes 16, 17, 18, 26, 27, 29, 30, 31, 32, 33 and 40 had exploded, apparently because of degradation. Those aluminum rods that could be found exhibited severe pitting, ascribed to acid attack caused by degradation of fluorocarbon 21. The remainder of tubes 9-40 were noticeably discolored. By the end of the four weeks, the remainder of the tubes the phosphorus content being 0.01% by weight of the mixture in each tube. The contents of these tubes are shown in the Table 2:

Table 2

| ETFE Material | Low Purity ETFE (97% ETFE, 3% THFA) | | | High Purity ETFE (99.6% ETFE, 0.4% THFA) | | |
|---|---|---|---|---|---|---|
| Temperature | 350° F 175–180° C | 400° F 200–205° C | 450° F 230–235° C | 350° F | 400° F | 450° F |
| triphenyl phosphite 0.1% by wt | 49–52 | 53–56 | 57–60 | 61–64 | 65–68 | 69–72 |
| triisodecyl phosphite 0.162% by wt | 73–76 | 77–80 | 81–84 | 85–88 | 89–92 | 93–96 |
| diphenyl isodecyl phosphite | 97–100 | 101–104 | 105–108 | 109–112 | 113–116 | 117–120 |

Table 2-continued

| ETFE Material | Low Purity ETFE (97% ETFE, 3% THFA) | High Purity ETFE (99.6% ETFE, 0.4% THFA) |
|---|---|---|
| 0.121% by wt | | |

A group of controls were prepared with triphenyl phosphite alone or with cyclohexanol. The contents are shown in the following Table:

Table 3

| Number | ETFE Low | ETFE High | Triphenylphosphite | Cyclohexanol |
|---|---|---|---|---|
| 121 & 122 | x | | 0.2% | |
| 123 & 124 | x | | 0.4% | |
| 125 & 126 | | x | 0.2% | |
| 127 & 128 | | x | 0.4% | |
| 129 & 130 | x | | 0.1% | 0.2% |
| 131 & 132 | | x | 0.1% | 0.2% |

A second set of controls was prepared with low purity ETFE alone in tubes 133 and 134, high purity ETFE alone in tubes 135 and 136 and fluorocarbon 21 alone in tubes 137–140.

Each of the tubes of Examples 49–120 was elevated to the indicated temperature. Each of the control tubes 121–140 was also elevated to 450° F (230°–235° C).

A third set of controls was prepared and kept at room temperature. Tubes 141 and 142 contined low purity ETFE alone, tubes 143 and 144 contained high purity ETFE alone, tubes 145–148 contain fluorocarbon 21 alone, tubes 149 and 150 contain low purity ETFE and fluorocarbon 21 and tubes 151 and 152 contained high purity ETFE in fluorocarbon 21. Tubes 141–152 were kept at room temperature.

A fourth set of controls, tubes 153–158, were prepared to show the effect of water on the system. The materials in these tubes as shown in the Table 4.

Table 4

| Number | ETFE low purity | ETFE high purity | Triphenyl-phosphite | Water |
|---|---|---|---|---|
| 153 and 154 | x | | 0.1% | 1% |
| 155 | x | | 0.2% | 1% |
| 156 and 157 | | x | 0.1% | 1% |
| 158 | | x | 0.2% | 1% |

Tubes 153–158 were kept at 450° F.

After 3 months, almost all of the 450° F samples had exploded. These included Examples 57–60, 69, 71, 81, 82, 84, 105–108 and 117–132. Yet even at 450° F, tubes 70, 72, 83 and 93–96 have survived three months with marked discoloration. Referring particularly to Examples 93–96, it can be seen that triisodecyl phosphite is especially effective in stabilizing high purity ETFE with fluorocarbon 21 for 3 months at 450° F, and should provide excellent stability to most of the preferred furan ring containing compounds with the preferred fluorocarbons at operating the temperatures of a heat activated heat pump for many years.

Furthermore, at 350° and 400° F all of the samples survived 3 months. These included tubes 49–56, 61–68, 73–80, 85–92, 97–104 and 109–116. Only the 400° F samples began to show discoloration toward the end of the 3 month period. These examples show that each of the above tribasic phosphite stabilizers are quite effective under anticipated maximum heat activated heat pump temperatures for several months, which corresponds to many years under operating conditions.

Each of the second and fourth set of controls also exploded within the first 3 months. This demonstrates that higher phosphite amounts, alone or with cyclohexanol or water impurities, does not appear to cause survival at prolonged exposures to temperatures as high as 450° F. Nevertheless, phosphite amounts from about 0.05% by weight to about 0.6% by weight are preferred, as giving sufficient stabilization.

EXAMPLES 159 and 160

Similar tubes were prepared with 85% t-butyl tetrahydrofurfurylether and 15% fluorocarbon 21. 0.2% triphenyl phosphite was added by weight. These samples were also heated to 450° F (230° C).

EXAMPLES 161–168

Compositions are prepared with the following ethers, fluorocarbons and phosphite stabilizers. The percentages are by weight.

| No. | Ethers* | wt % | Fluoro-carbons* | wt % | Phosphites $(R_1'O)(R_2'O)(R_3'O)P$ $R_1$ | $R_2$ | $R_3$ | wt % |
|---|---|---|---|---|---|---|---|---|
| 161 | ETFE | 70 | R22 | 29.9 | isodecyl | isodecyl | phenyl | 0.035 |
| 162 | t-BTFE | 90 | R21 | 9.9 | ethyl | nonyl | nonyl | 0.1 |
| 163 | n-BTFE | 65 | R23 | 34.8 | methyl | p-tolyl | p-tolyl | 0.2 |
| 164 | n-PTFE | 95 | R21 | 4.9 | phenyl | n-decyl | n-decyl | 0.1 |
| 165 | i-PTFE | 80 | R31 | 19.9 | dodecyl | dodecyl | dodecyl | 0.1 |
| 166 | ETFE | 65 | R123 | 34.95 | isodecyl | isodecyl | isodecyl | 0.65 |
| 167 | i-BTFE | 80 | R124 | 19 | methyl | methyl | tridecyl | 0.6 |
| 168 | ETFE | 69 | R21 | 30.6 | phenyl | n-propyl | p-ethyl phenyl | 0.4 |

*The furan ethers are ETFE-ethyl tetrahydrofurfuryl ether; PTFE-propyl tetrahydrofurfuryl ether; BTFE-butyl tetrahydrofurfuryl ether. The fluorocarbons are R-21 $CHCl_2F$; R-22 $CHClF_2$; R-23 $CHF_3$; R-31 $CH_2ClF$; R-123 $C_2HCl_2F_3$ (preferred isomer $CHCl_2CF_3$); R-124 $C_2HClF_4$ (either isomer $CHClFCF_3$ or $CHF_2CClF_2$); and R-133 $C_2H_2ClF_3$ (preferred isomer $CH_2ClCF_3$ known as R-133a). Each of the Examples 161–168 exhibit good thermic stability.

EXAMPLES 169–187

Compositions are prepared with 80% of the following furan derivatives, 19.9% of fluorocarbon 21 and 0.1% of the following phosphite stabilizers all by weight.

Furan Derivative

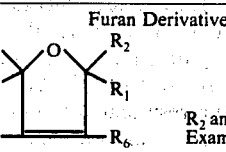

$R_2$ and $R_4$ are H in Examples 169-180

Phosphite Stabilizer $(R_1'O)(R_2'O)(R_3'O)P$

| No. | $R_1$ | $R_3$ | $R_5$ | $R_6$ | $R_1'$ | $R_2'$ | $R_3'$ |
|---|---|---|---|---|---|---|---|
| 169 | H | H | H | —CH$_2$OH | methyl | phenyl | phenyl |
| 170 | phenyl | —CH$_2$O(CH$_2$)$_4$CH$_3$ | H | H | —CH$_2$CH$_2$-phenyl | CH$_2$CH$_2$-phenyl | CH$_2$CH$_2$-phenyl |
| 171 | Cl | —(CH$_2$)$_5$phenyl | —CH$_2$OCH$_3$ | H | isodecyl | isodecyl | isodecyl |
| 172 | F | H | —CH$_2$OC(O)CH$_3$ | H | isooctyl | isooctyl | isooctyl |
| 173 | —(CH$_2$)$_2$OC(O)(CH$_2$)$_2$CH$_3$ | H | —CH$_2$OH | H | lauryl | lauryl | lauryl |
| 174 | —(CH$_2$)$_5$CH$_2$OCH$_3$ | H | n-butyl | H | stearyl | stearyl | stearyl |
| 175 | —OCH$_3$ | H | —O(CH$_2$)$_4$CH$_3$ | H | nonyl-phenyl | nonyl-phenyl | nonyl-phenyl |
| 176 | CH$_2$phenyl | H | H | H | phenyl | phenyl | isooctyl |
| 177 | H | —CH$_2$OCH$_3$ | H | CH$_2$CH$_2$ | phenyl | phenyl | isooctyl |
| 178 | H | H | H | —CH$_2$OCH$_3$ | phenyl | phenyl | phenyl |
| 179 | CH$_3$ | H | H | —CH$_2$OCH(CH$_3$)$_2$ | (CH$_2$)$_4$-phenyl | propyl-phenyl | propyl-phenyl |
| 180 | CH$_3$ | H | H | —(CH$_2$)$_3$CH$_2$OCH$_3$ | dimethyl-phenyl | phenyl | phenyl |

Furan Derivative

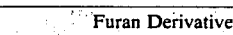

$R_{10}$ and $R_{12-14}$ are each H in Examples 181-184.

Phosphite Stabilizer $(R_1'O)(R_2'O)(R_3'O)P$

| No. | $R_7$ | $R_8$ | $R_9$ | $R_{11}$ | $R_1'$ | $R_2'$ | $R_3'$ |
|---|---|---|---|---|---|---|---|
| 181 | phenyl | H | H | —CH$_2$OCH$_2$CH$_3$ | isopropyl | phenyl | phenyl |
| 182 | —CH$_2$phenyl | H | CH$_3$ | —CH$_2$OC(CH$_3$)$_3$ | isooctyl | isooctyl | isooctyl |
| 183 | —CH$_2$CH$_3$ | H | H | —CH$_2$OCH(CH$_3$)CH$_2$CH$_3$ | phenyl | phenyl | isooctyl |
| 184 | CH$_2$OCH$_2$CH$_3$ | —CH$_3$ | H | —CH$_2$CH$_3$ | propyl | phenyl | isooctyl |

$R_8$ and $R_{13}$ are each H in Examples 185-187.

| No. | $R_7$ | $R_9$ | $R_{10}$ | $R_{11}$ | $R_{12}$ | $R_{14}$ | $R_1'$ | $R_2'$ | $R_3'$ |
|---|---|---|---|---|---|---|---|---|---|
| 185 | H | H | —OCH$_3$ | —OCH$_3$ | H | —CH$_2$OCH$_2$CH$_3$ | phenyl | phenyl | phenyl |
| 186 | H | H | H | H | —O(CH$_2$)$_4$CH$_3$ | H | methyl | methyl | isooctyl |
| 187 | methyl | n-butyl | H | H | —(CH$_2$)$_3$OCH$_2$CH$_3$ | H | isodecyl | isodecyl | isodecyl |

We claim:

1. A stabilized absorption composition comprising
   a. a fluorocarbon as refrigerant selected from the group consisting of monochlorodifluoromethane, dichloromonofluoromethane, trifluoromethane, monochloromonofluoromethane, dichlorotrifluoroethane, monochlorotetrafluoroethane, monochlorotrifluoroethane and mixtures thereof;
   b. an asymetrical furan derivative as absorbent of the formula:

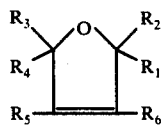

where $R_1$, $R_2$, $R_3$, $R_4$, $R_5$ and $R_6$ are each independently H, alkyl having 1-5 carbons, alkoxy having 1-5 carbons, phenyl, alkylene phenyl having 7-11 carbons, hydroxy alkyl having 1-5 carbons, alkoxy alkyl having 2-6 carbons, alkyl carboxylate having 2-6 carbons, fluorine or chlorine, provided that at least one of $R_1$, $R_2$, $R_3$, $R_4$, $R_5$ and $R_6$ has an oxygen atom which has a single bond to a carbon atom; or of the formula

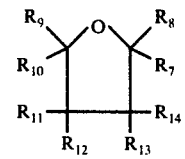

where $R_7$, $R_8$, $R_9$, $R_{10}$, $R_{11}$, $R_{12}$, $R_{13}$ and $R_{14}$ are each independently as defined above for $R_1$, $R_2$, $R_3$, $R_4$, $R_5$, and $R_6$, provided at least one of $R_7$, $R_8$, $R_9$, $R_{10}$, $R_{11}$, $R_{12}$, $R_{13}$ and $R_{14}$ has an oxygen atom which has a single bond to a carbon atom; and an effective amount of a stabilizer of the formula $(R_1'O)(R_2'O)(R_3'O)P$ wherein $R_1'$, $R_2'$ and $R_3'$ are each independently alkyl, alkenyl, phenyl, alkylene phenyl, alkylene alkylphenyl, or alkylphenyl.

2. A stabilized composition according to claim 1 and comprising about 4% to about 6% of said fluorocarbon by weight of said furan derivative.

3. A stabilized composition according to claim 2 having about 0.05% to about 3.0% of said stabilizer by weight of said furan derivative.

4. A stabilized composition according to claim 3 having about 0.05% to about 1.0% of said stabilizer by weight of said furan derivative.

5. A stabilized composition according to claim 1 wherein said fluorocarbon is dichloromonofluoromethane.

6. A stabilized composition according to claim 1 wherein asymmetrical furan derivative is of the formula

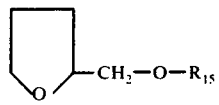

where $R_{15}$ is alkyl having 1-5 carbons.

7. A stabilized composition as claimed in claim 6 wherein $R_{15}$ is alkyl having 2-4 carbons.

8. A stabilized composition according to claim 7 wherein said furan derivative is ethyl tetrahydrofurfuryl ether.

9. A stabilized composition according to claim 7 wherein said furan derivative is t-butyl tetrahydrofurfuryl ether.

10. A stabilized composition according to claim 1 wherein $R_1'$, $R_2'$ and $R_3'$ each have 1-20 carbons.

11. A stabilized composition according to claim 10 wherein $R_1'$, $R_2'$ and $R_3'$ each have 6-14 carbons.

12. A stabililized composition according to claim 11 wherein said stabilizer $R_1'$, $R_2'$ and $R_3'$ are each independently alkyl having 6-14 carbons, phenyl, alkylphenyl having 7-14 carbons, alkylene phenyl having 7-14 carbons or alkylene alkylphenyl having 8-14 carbons.

13. A stabilized composition according to claim 12 wherein said stabilizer $R_1'$, $R_2'$ and $R_3'$ are each independently isodecyl or phenyl.

14. A stabilized composition according to claim 13 wherein the stabilizer is triisodecyl phosphite.

15. A method of absorption heating which comprises
a. releasing heat of solution in the vicinity of an area to be heated by absorbing a fluorocarbon in an asymmetrical furan derivative containing a stabilizer to form the composition of claim 1, heating the resultant solution to release said fluorocarbon from said furan derivative, condensing released fluorocarbon in the vicinity of the area to be heated to form liquid fluorocarbon, evaporating the liquid fluorocarbon at a location removed from the vicinity of the area to be heated and returning the evaporated fluorocarbon to the vicinity of the area to be heated for reabsorption into said solvent furan derivative.

16. The method of claim 15 wherein the furan derivative and stabilizer remain liquid throughout said method.

17. The method of claim 15 wherein the fluorocarbon is dichloromonofluoromethane.

18. The method of claim 15 wherein the furan derivative is an alkyl tetrahydrofurfuryl ether, said alkyl having 1-5 carbons.

19. The method of claim 18 wherein the furan derivative said alkyl has 2-4 carbons.

20. The method of claim 19 wherein the furan derivative is ethyl tetrahydrofurfuryl ether.

21. The method of claim 19 wherein the furan derivative is t-butyl tetrahydrofurfuryl ether.

22. The method of claim 19 wherein the stabilizer $R_1'$, $R_2'$ and $R_3'$ each have 1-20 carbons.

23. The method of claim 15 wherein the solution is heated to from about 250° to about 450° F to release the fluorocarbon.

24. The method of claim 15 wherein said absorption takes place at a temperature from about 90° to about 130° F.

* * * * *

UNITED STATES PATENT AND TRADEMARK OFFICE
CERTIFICATE OF CORRECTION

PATENT NO. : 4,072,027

DATED : February 7, 1978

INVENTOR(S) : Morris B. Berenbaum et al.

It is certified that error appears in the above-identified patent and that said Letters Patent are hereby corrected as shown below:

Column 3, line 63, delete comma after "triisooctyl."

Column 3, line 65, "properties" should read -- phosphites --.

Column 10, line 61, "6%" should read -- 60% --.

Signed and Sealed this

First Day of August 1978

[SEAL]

Attest:

RUTH C. MASON
Attesting Officer

DONALD W. BANNER
Commissioner of Patents and Trademai